United States Patent [19]

Liebert et al.

[11] 4,117,025
[45] Sep. 26, 1978

[54] PROCESS FOR PURIFYING DIOLEFIN

[75] Inventors: Timothy C. Liebert; William A. McClintock, both of Bartlesville, Okla.

[73] Assignee: Phillips Petroleum Company, Bartlesville, Okla.

[21] Appl. No.: 817,393

[22] Filed: Jul. 20, 1977

[51] Int. Cl.² .............................................. C07C 7/00
[52] U.S. Cl. ............................ 260/681.5; 260/666 B; 260/666 D
[58] Field of Search ............. 260/681.5, 666 B, 666 D

[56] References Cited

U.S. PATENT DOCUMENTS

| 2,355,392 | 8/1944 | Oberfell | 260/681.5 |
|---|---|---|---|
| 3,377,397 | 4/1968 | Maxfield | 260/666 B |
| 3,448,129 | 6/1969 | Maxfield | 260/429 |
| 3,655,793 | 4/1972 | Myers | 260/666 B |
| 3,751,508 | 8/1973 | Fujiso et al. | 260/677 H |
| 3,957,894 | 5/1976 | Saeki et al. | 260/666 B |

Primary Examiner—Veronica O'Keefe

[57] ABSTRACT

A process for the separation of a diolefin from a mixture thereof with other hydrocarbons having boiling points close to that of the diolefin, comprising subjecting the mixture of hydrocarbons to reaction conditions which will dimerize the diolefin, separating effluent of the dimerization into a first heavy fraction comprising the diolefin dimer and materials of higher boiling point than the diolefin dimer and a first light fraction comprising hydrocarbons having lower boiling points than the diolefin dimer, separating the first heavy fraction into a second heavy fraction comprising materials having higher boiling points than the diolefin dimer and a second light fraction comprising diolefin dimer, passing at least a portion of the second light fraction along with steam through a cracking zone under conditions sufficient to cause the diolefin dimer to be converted to the starting diolefin monomer, using at least a portion of the second heavy fraction as fuel burned to supply heat to the cracking zone, cooling the effluent from the cracking zone to recover a water phase, converting at least a portion of the recovered water to steam and recycling at least a portion of the steam through the cracking zone, and subjecting at least a portion of the dewatered cracking effluent to distillation to recover a hydrocarbon composition which has a greater concentration of the diolefin than did the original mixture of hydrocarbons.

7 Claims, 1 Drawing Figure

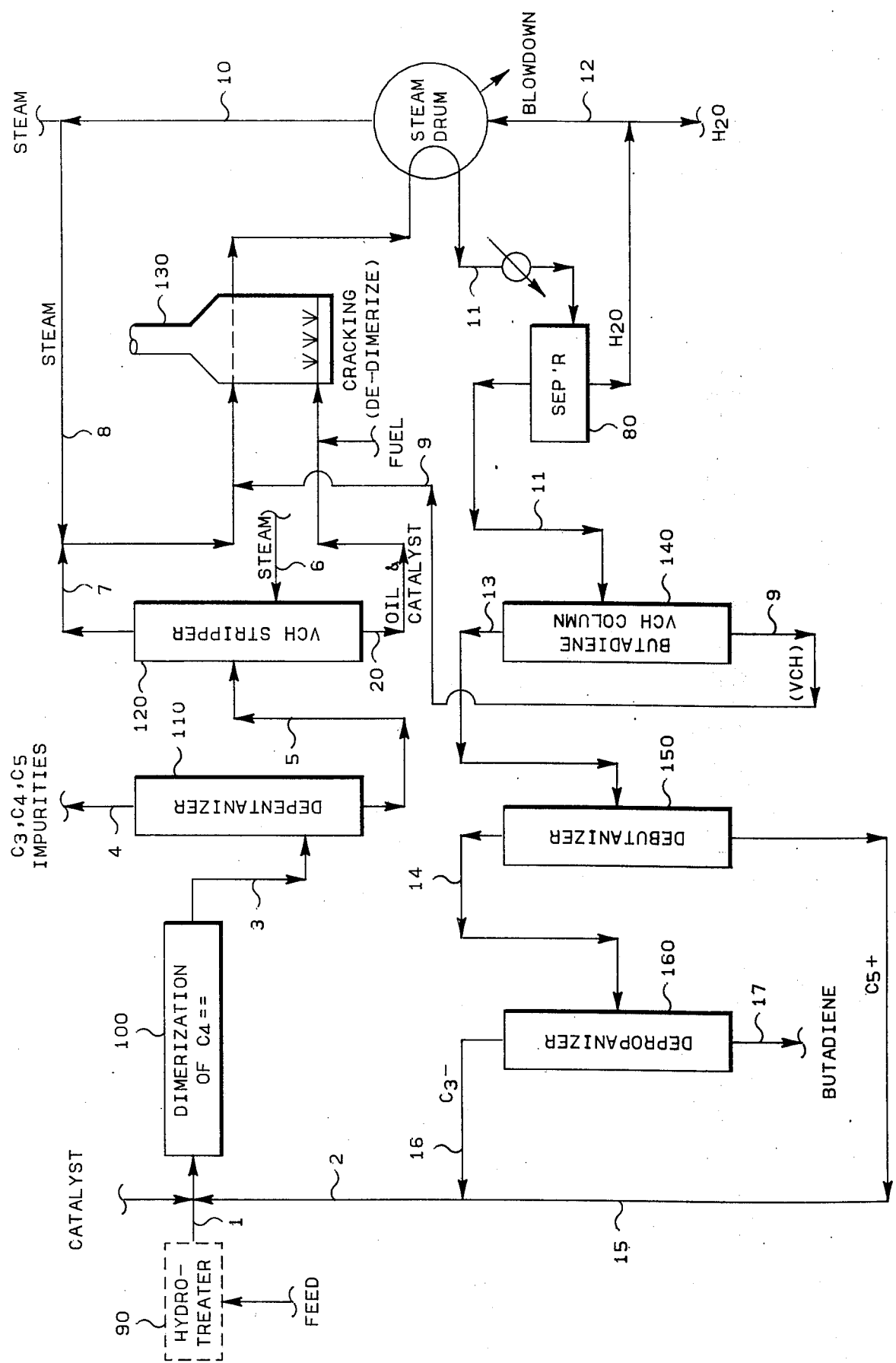

PROCESS FOR PURIFYING DIOLEFIN

This invention relates to a process for the separation and concentration of diolefinic hydrocarbons from mixtures containing other hydrocarbons. In another aspect this invention relates to the separation of diolefins by a process in which said diolefins are successively converted to polymers of relatively low molecular weight, separated in polymer form by distillation or other suitable methods, and finally recovered as monomeric diolefins by a depolymerization treatment.

An object of this invention is to separate diolefins from mixtures containing other hydrocarbons such as paraffins and monoolefins.

Another object of this invention is to produce diolefins in concentrated form suitable for use in chemical conversion processes.

Another object of this invention is to remove diolefins from hydrocarbon mixtures such as are produced by cracking operations.

Another object of this invention is to separate diolefins in such a manner that the by-products of the process are used to improve the efficiency of the process.

The manufacture of butadiene, isoprene, and similar conjugated diolefins from petroleum hydrocarbons by cracking, dehydrogenation, and similar methods is handicapped by the fact that the desired diolefin generally is obtained in a very dilute form, in admixture with other hydrocarbons. For example, the four-carbon-atom fraction of gases from vapor phase oil cracking stills will usually contain less than 20 volume percent of butadiene. Pyrolysis of butane gas under conventional conditions likewise gives very low percentages of butadiene. As a rule, a similar fraction from other cracking processes will contain much smaller percentages of butadiene.

In commercial processes utilizing diolefins it is very advantageous, if not economically imperative, to have the diolefins in concentrated form. For example, in the conversion of butadiene to synthetic rubbers, such as polybutadiene, or by copolymerization with monomers such as styrene and other costly organic derivatives, it is generally uneconomical to start with a butadiene feedstream of less than 90–95 percent purity. For other processes and conditions, it may be economical to use lower concentrations of butadiene, but generally higher concentrations than can be produced directly are desired.

In accordance with the present invention a diolefin is separated from a mixture thereof with other hydrocarbons having boiling points close to the boiling point of the diolefin by subjecting the hydrocarbon mixture to conditions which will dimerize the diolefin, separating effluent of the dimerization into a first heavy fraction comprising the diolefin dimer and materials of higher boiling point than the diolefin dimer and a first light fraction comprising hydrocarbons having lower boiling points than the diolefin dimer, separating the first heavy fraction into a second heavy fraction comprising materials having higher boiling points than the diolefin dimer and a second light fraction comprising the diolefin dimer, passing at least a portion of the second light fraction along with steam through a cracking zone under conditions sufficient to de-dimerize the diolefin dimer, using at least a portion of the second heavy fraction as fuel for supplying heat for the cracking zone, cooling the effluent from the cracking zone to recover a water phase, separating the water phase from the hydrocarbon phase, converting at least a portion of the separated water into steam, directing at least a portion of the steam into and through the cracking zone, and subjecting at least a portion of the hydrocarbon phase to distillation to recover a hydrocarbon composition which has a greater concentration of the diolefin than the original mixture of hydrocarbons subjected to the above described treatments.

In accordance with a preferred embodiment of the present invention the hydrocarbon phase of the effluent from the cracking zone is separated into a third heavy fraction containing a portion of the diolefin dimer which was not converted back to the diolefin, and materials having higher boiling points and a third light fraction containing materials having boiling points lower than that of the diolefin dimer, at least a portion of the third heavy fraction is recycled back to and through the cracking zone, at least a portion of the third light fraction is separated into a fourth light fraction containing the diolefin and hydrocarbons having lower boiling points than the diolefin and a fourth heavy fraction containing materials having higher boiling points than the diolefin, and at least a portion of the fourth light fraction is separated into a fifth light fraction containing materials having lower boiling points than the diolefin and a fifth heavy fraction containing the diolefin.

The present invention is suited for the concentration of any diolefinic hydrocarbons which can be dimerized and de-dimerized in accordance with this invention. Examples of diolefins which should be suitable include, but are not limited to 1,3-pentadiene, 1,3-butadiene, and isoprene. The present invention is particularly suitable for the purification of $C_4$ conjugated diolefins.

While this invention may be applied to hydrocarbon mixtures containing hydrocarbons of widely differing boiling points, it is particularly applicable to a mixture in which substantially all of the hydrocarbons have boiling points within about 30° F of the boiling point of the diolefin, and even more so to a mixture in which substantially all of the hydrocarbons have boiling points within about 15° F of the boiling point of the diolefin. For example to obtain concentrated 1,3-butadiene it would be preferable to dimerize a hydrocarbon fraction that boils in the range of about 15° F to about 30° F and to obtain a concentrated isoprene it would be preferable to dimerize a hydrocarbon fraction that boils in the range of about 85° F to 105° F.

The dimerization can be conducted in any manner which results in the dimerization of the diolefin in the presence of other hydrocarbons having boiling points close to that of the diolefin.

One suitable dimerization technique involves subjecting the mixture of hydrocarbons to a temperature in the range of about 300° to about 900° F until dimerization of the diolefin occurs. The rate of reaction increases with an increase of temperature. For this elevated temperature technique elevated pressures are generally advantageous. Pressures within the range of atmospheric to around 500 pounds per square inch gauge are particularly effective. Higher pressures may be employed where desirable. At the more elevated pressures the diolefins tend to combine to form products of higher molecular weight than the dimers. Accordingly pressures are preferably employed which minimize such oligomerization or polymerization. Solid contact catalysts such as fuller's earth, bauxite, activated alumina, and silica gel favor the formation of the dimer in both liquid and vapor phases. In this technique it is also frequently advantageous to use inhibitors which repress the formation of higher polymers. This is particularly so when the lower temperature ranges are employed. At temperatures below about 300° F unless special catalyst systems are employed the formation of higher diolefin polymers is generally favored over the production of diolefin dimer. Also the presence of catalysts and chemicals which tend to react with the diolefin to yield higher polymers should be minimized. Examples of such materials include oxygen, peroxides, alkali metals, acids, and metal halides.

A more preferred method of dimerization is one in which the diolefin can be dimerized at temperatures lower than about 300° F without the formation of any substantial amounts of higher polymers. Several such techniques are known in the art and others probably will be discovered. These techniques involve the employment of special organo-metallic dimerization catalysts which have been discovered to convert the diolefin to dimer with very little, if any, higher polymer formation even at temperatures below about 300° F. Examples of such dimerization techniques are disclosed in U.S. Pat. No. 3,377,397, Perry L. Maxfield patentee; U.S. Pat. No. 3,448,129, Perry L. Maxfield patentee; U.S. Pat. No. 3,655,793, Charles L. Myers patentee; U.S. Pat. No. 3,767,593, Charles L. Myers patentee; and U.S. Pat. No. 3,957,894, Kenji Saeki and Tetsuv Hayashi patentees. The disclosures of these patents are incorporated herein by reference. The optimization of such dimerization processes, i.e., selection of catalyst concentration and dimerization conditions, is well within the routine skill of those skilled in the art.

Inasmuch as some of the diolefin dimerization catalysts may be deactivated somewhat by hydrocarbons containing acetylenic functionality, it is sometimes preferable to precede the dimerization step by a selective hydrotreatment which will reduce the level of acetylenic functionality without any significant amount of hydrogenation of the diolefin unsaturation. Such techniques are known in the art. An example of one such selective hydrotreatment is disclosed in U.S. Pat. No. 3,751,508, Tokuo Fryiso and Tadashi Ohmori patentees. The disclosure of that patent is incorporated herein by reference.

Since the dimers which form boil at much higher temperatures than the original diolefin, ordinary distillation can be employed to obtain a first light fraction containing the non-diolefin hydrocarbons which have boiling points close to that of the diolefin and a first heavy fraction containing the diolefin dimer and materials having higher boiling that that of the diolefin dimer. Of course, any suitable means of obtaining such a separation can be employed. Also, any suitable means can be employed to separate the first heavy fraction into a second light fraction containing the diolefin dimer and a second heavy fraction containing materials having higher boiling points than the diolefin dimer. Preferably this is done using a steam stripping technique.

The de-dimerization can be accomplished using any steam thermal cracking process which will convert the dimer to the corresponding monomeric diolefin. Preferably the cracking process is carried out under conditions to minimize the formation of by-products having boiling points close to that of the monomeric diolefin. Preferably the cracking is at least about 50 to 97 percent selective to the monomeric diolefin. Temperatures of about 900° to about 1300° F are generally suitable for the de-dimerization. Considerably higher temperatures may be employed if the heating time is made sufficiently short to limit ordinary thermal decomposition. And of course the temperature employed will be somewhat dependent upon the type of diolefin dimer that is to be de-dimerized. Generally the cracking is carried out at pressures in the range of about 50 to about 250 psig, although any suitable pressure can be employed. The amount of steam employed can also vary widely, generally the ratio of the pounds of total steam to pounds of hydrocarbon charge to the cracking zone will be in the range of about 1:2 to about 3:1.

Any suitable cracking catalysts may also be used in the cracking step. Examples of known cracking catalysts include silver, copper, platinum, and iron, generally in the form of reduced oxides, and oxides of calcium and magnesium.

The effluent from the cracking zone can be cooled by any suitable heat exchange means to cause the condensation of water. A portion of the water recovered from the effluent from the cracking zone can be reheated to produce steam for the cracking zone. In a preferred embodiment the heat of the effluent from the cracking zone is employed in the reheating of the water recovered from previous portions of that effluent stream. After the condensed water has been removed, the cracked products are subjected to separations as above described. The separation of the various fractions of the cracking effluent can be readily accomplished by distillation.

The present invention will now be described with reference to the flow diagram of FIG. 1. FIG. 1 is an illustration of one embodiment of the instant invention. For the purpose of illustration the process will be described with reference to obtaining purer 1,3-butadiene from a hydrocarbon mixture containing 1,3-butadiene. The hydrocarbon mixture or feed, after being optionally passed through the hydrotreater 90 for selective removal of undesirable acetylenic functionality, is passed through conduit means 1 into a dimerization reactor 100, such as a plug flow reactor, along with a suitable organo-metallic dimerization catalyst, preferably in a suitable diluent. In the dimerization reactor butadiene is converted to vinylcyclohexene. The effluent from the dimerization reactor is passed via conduit means 3 into a distilling column 110 operated so that the overhead 4 comprises pentanes and lighter hydrocarbons and the bottoms comprise hydrocarbons having higher boiling points than pentanes. The bottoms 5 from the column 110 is passed to a steam stripping column 120 having steam added via conduit means 6. The overhead 7 from the column 120, comprising vinylcyclohexene, is combined with additional steam supplied via conduit means 8 and is passed into a cracking or de-dimerizing furnace 130. The bottoms from the vinylcyclohexene steam stripper column 120 comprises dimerization catalyst residue and hydrocarbons of higher boiling point than vinylcyclohexene. The bottoms from the column 120 is removed via conduit means 20 and at least a portion thereof is employed to supplement the fuel burned to heat the cracking furnace 130. In the furnace 130 vinylcyclohexene is de-dimerized to butadiene. Effluent from the furnace 130 comprising butadiene is passed through conduit means 11' to decanting means 80. Before reaching the decanting means 80 the effluent from the cracking furnace 130 is subjected to heat exchange to produce steam in the steam drum for the cracking furnace and additional cooling of the effluent which causes water in the effluent to condense. The condensed water collects in the decanter 80 and at least a portion of that water is passed from there via conduit means 12 to a steam drum wherein the water is converted back to steam which can be passed via conduit means 10 to conduit means 8 which supplies steam for the cracking furnace 130.

The hydrocarbon phase of the effluent from the cracking furnace passes from the decanter 80 via conduit means 11 into a butadiene-vinylcyclohexene fractionation column 140. Bottoms from the column 140 comprising vinylcyclohexene, i.e., uncracked dimer, are passed via conduit means 9 to conduit means 7 for recycling through the cracking furnace 130 with vinylcyclohexene overhead from the stripper 120.

The overhead from column 140 is sent via conduit means 13 to a fractionation column 150 referred to in FIG. 1 as a debutanizer. Bottoms from column 150, comprising hydrocarbons having higher boiling points than butadiene are removed via conduit means 15. The overhead from column 150, comprising butadiene and hydrocarbons having lower boiling points than butadiene, is passed via conduit means 14 to another fractionation column 160, referred to as a depropanizer in FIG. 1. The overhead from column 160, comprising hydrocarbons having lower boiling points than butadiene, is removed via conduit means 16. The bottoms from column 160 comprises the purer butadiene product which is removed via conduit means 17.

Hydrocarbon fractions in conduit means 16 and 15 are combined and passed via conduit means 2 for recycling with additional feed 1 that is to be purified.

With reference to the system illustrated in FIG. 1, a calculated example of the system operation will now be provided. For the purpose of this example the conditions in the process vessels are as follows:

| | | |
|---|---|---|
| (100) Dimerization Reactor: | | |
| Pressure, psia, | 120 | (828 kPa) |
| Temperature, ° F, | 175 | (79.44° C) |
| Residence time, min., | 20 | |
| (110) Depentanizer: | | |
| Pressure, psia, | | |
| Top, | 80 | (552 kPa) |
| Bottom, | 83 | (573 kPa) |
| Temperature, ° F, | | |
| Top, | 127 | (52.78° C) |
| Bottom, | 410 | (210° C) |
| (120) Vinylcyclohexane Stripper: | | |
| Pressure, psia, | 130 | (897 kPa) |
| Temperature, ° F, | 365 | (185° C) |
| (130) Cracking Furnace: | | |
| Pressure, psia, | 130 | (897 kPa) |
| Temperature, ° F, | 1000 | (537.78° C) |
| Wt. Ratio, Total Steam/VCH, | 1.2:1 | |
| (140) Butadiene-Vinylcyclohexane Column: | | |
| Pressure, psia, | | |
| Top, | 100 | (690 kPa) |
| Bottom, | 105 | (725 kPa) |
| Temperature, ° F, | | |
| Top, | 139 | (59.5° C) |
| Bottom, | 325 | (162.78° C) |
| (150) Debutanizer: | | |
| Pressure, psia, | | |
| Top, | 85 | (587 kPa) |
| Bottom, | 87 | (600 kPa) |
| Temperature, ° F, | | |
| Top, | 127 | (52.78° C) |
| Bottom, | 163 | (72.78° C) |
| (160) Depropanizer: | | |
| Pressure, psia, | | |
| Top, | 70 | (483 kPa) |
| Bottom, | 71 | (490 kPa) |
| Temperature, ° F, | | |
| Top, | 92 | (33.33° C) |
| Bottom, | 115 | (46.11° C) |

With the process operated under such conditions calculations indicate that in a continuous operation the components in the various streams would be expected to be approximately as set forth in the following table.

TABLE I

| Stream Number | 1 | 2 | 3 | 4 | 5 | 6 | 7 | 8 | 9 | 10 |
|---|---|---|---|---|---|---|---|---|---|---|
| Component | | | | | | | | | | |
| Propylene | 301 | 302 | 603 | 603 | — | — | — | — | — | — |
| Methyl Acetylene | 6 | — | 6 | 6 | — | — | — | — | — | — |
| Isobutane | 361 | — | 361 | 361 | — | — | — | — | — | — |
| Isobutene | 13,369 | — | 13,369 | 13,369 | — | — | — | — | — | — |
| Butene-1 | 8,250 | — | 8,250 | 8,250 | — | — | — | — | — | — |
| 1,3-Butadiene | 28,485 | 295 | 288 | 288 | — | — | — | — | — | — |
| Normal Butane | 1,445 | — | 1,445 | 1,445 | — | — | — | — | — | — |
| Trans-2-Butene | 3,493 | — | 3,493 | 3,493 | — | — | — | — | — | — |
| Cis-2-Butene | 2,891 | — | 2,891 | 2,891 | — | — | — | — | — | — |
| Vinyl Acetylene | 1,024 | — | 1,024 | 1,024 | — | — | — | — | — | — |
| Ethyl Acetylene | 120 | — | 120 | 120 | — | — | — | — | — | — |
| 1,2-Butadiene | 181 | — | 181 | 181 | — | — | — | — | — | — |
| Pentenes | 301 | 485 | 786 | 782 | 4 | — | 4 | — | — | — |
| Vinylcyclohexene[a] | — | 13 | 28,505 | — | 28,505 | — | 28,505 | — | 28,505 | — |
| Total | 60,277 | 1,095 | 61,322 | 32,813 | 28,509 | — | 28,509 | — | 28,505 | — |
| Catalyst and Carrier[b] | 250 | — | 250 | — | 250 | — | — | — | — | — |
| Water/Stream | — | 342 | 342 | 342 | — | 24,956 | 24,956 | 43,425 | — | 44,508 |

| Stream Number | 11 | 12 | 13 | 14 | 15 | 16 | 17 |
|---|---|---|---|---|---|---|---|
| Component | | | | | | | |
| Propylene | 354 | — | 354 | 354 | — | 302 | 52 |
| Methyl Acetylene | — | — | — | — | — | — | — |
| Isobutane | — | — | — | — | — | — | — |
| Isobutene | — | — | — | — | — | — | — |
| Butene-1 | — | — | — | — | — | — | — |
| 1,3-Butadiene | 27,637 | — | 27,637 | 27,497 | 140 | 155 | 27,342 |
| Normal Butane | — | — | — | — | — | — | — |
| Trans-2-Butene | — | — | — | — | — | — | — |
| Cis-2-Butene | — | — | — | — | — | — | — |
| Vinyl Acetylene | — | — | — | — | — | — | — |
| Ethyl Acetylene | — | — | — | — | — | — | — |
| 1,2-Butadiene | — | — | — | — | — | — | — |
| Pentenes | 505 | — | 505 | 20 | 485 | — | 20 |
| Vinylcyclohexane[a] | 28,518 | — | 13 | — | 13 | — | — |
| Total | 57,014 | — | 28,509 | 27,871 | 638 | 457 | 27,414 |
| Catalyst and Carrier[b] | — | — | — | — | — | — | — |

TABLE I-continued

| Water/Stream | — | 53,410 | 342 | 342 | — | 342 | — |

[a] 4-Vinylcyclohexene-1
[b] [(C₃H₅)(NO)₂Fe]₂SnCl₂ (U.S. Pat. No. 3,448,129) - 11.4 pounds of catalyst in 238.6 pounds of vinylcyclohexene per hour.

It should be noted that FIG. 1 and the foregoing description regarding it have been provided to serve as an illustration of an embodiment of the invention and should not be construed as unduly limiting the present invention.

What is claimed is:

1. A process for the separation of a diolefin from a mixture of hydrocarbons having boiling points close to that of the diolefin comprising subjecting the hydrocarbon mixture to conditions which will dimerize the diolefin, separating the effluent of the dimerization into a first heavy fraction comprising diolefin dimer and materials of higher boiling point than the diolefin dimer and a first light fraction comprising hydrocarbons having lower boiling points than the diolefin dimer, separating the first heavy fraction into a second heavy fraction comprising materials having higher boiling points than the diolefin dimer and a second light fraction comprising a diolefin dimer, passing the second light fraction along with steam through a cracking zone under conditions sufficient to de-dimerize the diolefin dimer, using at least a portion of the second heavy fraction as fuel for supplying heat for the cracking zone, cooling the effluent from the cracking zone to recover a water phase, separating the water phase from the hydrocarbon phase, converting at least a portion of the separated water into steam, directing the steam into and through the cracking zone, and subjecting at least a portion of the hydrocarbon phase to distillation so that a hydrocarbon composition is isolated which has a greater concentration of the diolefin than the original mixture of hydrocarbons.

2. A process according to claim 1 wherein the diolefin dimer and materials having boiling points greater than that of the diolefin dimer are separated from the effluent from the cracking zone and recycled to the cracking zone.

3. A process according to claim 1 further comprising separating the hydrocarbon phase of the effluent from the cracking zone into a third heavy fraction containing the diolefin dimer and materials having higher boiling points than the diolefin dimer and a third light fraction containing materials having boiling points lower than that of the diolefin dimer, recycling the third heavy fraction back to the cracking zone, separating the third light fraction into a fourth light fraction containing the diolefin and hydrocarbons having lower boiling points than the diolefin and a fourth heavy fraction containing materials having higher boiling points than the diolefin, and separating the fourth light fraction into a fifth light fraction containing materials having lower boiling points than the diolefin and a fifth heavy fraction containing the diolefin.

4. A process according to claim 3 wherein the diolefin is 1,3-butadiene.

5. A process according to claim 4 wherein the fourth heavy fraction and the fifth light fraction are recycled for dimerization.

6. A process according to claim 5 wherein the dimerization is conducted by contacting the hydrocarbon mixture with an organo-metallic dimerization catalyst system in a suitable diluent at a temperature of below about 300° F.

7. A process according to claim 6 wherein said first heavy fraction is separated into said second heavy fraction and said second light fraction by steam stripping.

* * * * *

UNITED STATES PATENT AND TRADEMARK OFFICE
CERTIFICATE OF CORRECTION

PATENT NO. : 4,117,025
DATED : September 26, 1978
INVENTOR(S) : Timothy C. Liebert and William A. McClintock It is certified that error appears in the above-identified patent and that said Letters Patent are hereby corrected as shown below:

Column 7, line 32, after "directing" and before "the" insert
--- at least a portion of ---.

Signed and Sealed this

Thirteenth Day of March 1979

[SEAL]

Attest:

RUTH C. MASON
Attesting Officer

DONALD W. BANNER
Commissioner of Patents and Trademarks